United States Patent
Deane

(12) 
(10) Patent No.: US 6,312,675 B1
(45) Date of Patent: Nov. 6, 2001

(54) HAIR CLEANER

(76) Inventor: Jeffrey Alan Deane, 6444 Fountain Ave., Hollywood, CA (US) 90028

(*) Notice: Subject to any disclaimer, the term of this patent is extended or adjusted under 35 U.S.C. 154(b) by 0 days.

(21) Appl. No.: 09/661,966

(22) Filed: Sep. 14, 2000

(51) Int. Cl.$^7$ ................ A61K 7/06; A61K 7/11; A61K 35/78; A61K 39/385; A01N 65/00

(52) U.S. Cl. ................ 424/70.1; 424/70.11; 424/74; 424/725; 424/735; 424/744; 424/747; 424/750; 424/775; 424/776; 510/119

(58) Field of Search .................. 424/70.1, 775, 424/725, 735, 744, 747, 750, 776, 195.1, 74, 70.11; 510/119

(56) References Cited

U.S. PATENT DOCUMENTS

| | | |
|---|---|---|
| 4,581,230 | 4/1986 | Grollier et al. . |
| 4,743,442 | 5/1988 | Raaf et al. . |
| 5,217,711 | 6/1993 | De Olivera . |
| 5,354,906 | 10/1994 | Weitemeyer . |
| 5,405,609 | 4/1995 | Sanchez . |
| 5,415,857 | 5/1995 | Robbins et al. . |
| 5,658,868 | 8/1997 | Esfandiari et al. . |
| 5,770,206 | 6/1998 | Nichilicchia . |
| 5,840,249 | 11/1998 | Bendiner . |
| 5,925,615 | 7/1999 | Kern et al. . |
| 5,942,479 | 8/1999 | Frankenbach et al. . |

Primary Examiner—Christopher R. Tate
Assistant Examiner—Michele C. Flood
(74) Attorney, Agent, or Firm—Norton R. Townsley

(57) ABSTRACT

A hair cleanser of the following formula: 5.00 to 10.00% by weight aloe vera gel; 2.00 to 5.00% by weight glycerin; 1.00 to 3.00% by weight behentrimonium chloride; 1.00 to 3.00% by weight stearamidepropyl dimethyamine; 1.00 to 3.00% by weight cetyl alcohol; 1.00 to 3.00% by weight emulsifying wax; 0.10 to 1.00% by weight panthenol; 0.10 to 1.00% by weight trimethylsilylamodimethicone; 0.10 to 1.00% by weight hydrolyzed whole wheat protein 0.10 to 1.00% by weight PEG-60 almond glycerides; 0.10 to 0.50% by weight menthol; 0.10 to 0.50% by weight peppermint oil;; 0.10 to 0.50% by weight sweet almond oil; 0.10 to 0.50% by weight chamomile extract; 0.10 to 0.50% by weight cherry bark extract; 0.10 to 0.50% by weight calendula extract; 0.10 to 0.50% by weight rosemary extract; 0.10 to 0.50% by weight citric acid; 0.10 to 0.50% by weight methylchoroisothiazolinone and methyliosothiazolinone; 0.10 to 0.50% by weight fragrance; and water.

2 Claims, No Drawings

HAIR CLEANER

BACKGROUND OF THE INVENTION

The present invention relates to the field of cosmetic treatments and more particularly to cleansers for the hair.

It is common practice nowadays to wash the hair with a shampoo and then to apply what is called a conditioner or conditioning treatment. The shampoo is a mixture of chemicals intended to remove dirt, oil and sweat from the hair and scalp. The chemicals used in shampoos are necessarily harsh removing essential oils and leaving the hair dry, dull and unmanageable. Shampoos frequently contain sodium lauryl sulfonate. Conditioners or conditioning treatments are intended to replace the oils washed out of the hair by shampoos. It is the job of conditioners to make the cleaned hair shiny and manageable.

It does not make much sense to harshly cleanse hair so that essential oils are removed and then to replace these oils. It would make much better sense to utilize a hair cleanser that does not remove oils in the first place. Development of a hair cleanser which can clean the hair without removing essential oils represents a great improvement in the field of hair treatments and satisfies a long felt need of the public.

SUMMARY OF THE INVENTION

The present invention is a hair cleanser which cleanses the hair but does not remove essential oils. The preferred formulation is:

| | |
|---|---|
| Water | to make 100.00 weight % |
| Aloe Vera Gel | 5.00 to 10.00 |
| Glycerin | 2.00 to 5.00 |
| Behentrimonium chloride | 1.00 to 3.00 |
| Stearamidepropyl dimethyamine | 1.00 to 3.00 |
| Cetyl alcohol | 1.00 to 3.00 |
| Emulsifying wax | 1.00 to 3.00 |
| Panthenol | 0.10 to 1.00 |
| Trimethylsilyamodimethicone | 0.10 to 1.00 |
| Hydrolyzed whole wheat protein | 0.10 to 1.00 |
| PEG[1]-60 almond glycerides | 0.10 to 1.00 |
| Menthol | 0.10 to 0.50 |
| Peppermint oil | 0.10 to 0.50 |
| Sweet almond oil | 0.10 to 0.50 |
| Chamomile extract | 0.10 to 0.50 |
| Cheny bark extract | 0.10 to 0.50 |
| Calendula extract | 0.10 to 0.50 |
| Rosemary extract | 0.10 to 0.50 |
| Citric acid | 0.10 to 0.50 |
| Methylchoroisothiazolinone and methyl-isothiazolinone | 0.10 to 0.50 |
| Fragrance | 0.10 to 0.50 |

[1]Polyethylene glycol

The present invention does not contain harsh chemicals. Instead it can be thought of as a mixture of conditioners. It has been found experimentally that this invention cleanses the hair and leaves the hair shinier, with more body, and more manageable.

An appreciation of the other aims and objectives of the present invention and an understanding of it may be achieved by referring to the accompanying description of a preferred embodiment.

DETAILED DESCRIPTION OF THE PREFERRED EMBODIMENT

The present invention is a hair cleanser having the following formulation:

| | |
|---|---|
| Water | to make 100.00 weight % |
| Aloe Vera Gel | 5.00 to 10.00 |
| Glycerin | 2.00 to 5.00 |
| Behentrimonium chloride | 1.00 to 3.00 |
| Stearamidepropyl dimethyamine | 1.00 to 3.00 |
| Cetyl alcohol | 1.00 to 3.00 |
| Emulsifying wax | 1.00 to 3.00 |
| Panthenol | 0.10 to 1.00 |
| Trimethysilylamodimethacone | 0.10 to 1.00 |
| Hydrolyzed whole wheat protein[2] | 0.10 to 1.00 |
| PEG-60 almond glycerides[2] | 0.10 to 1.00 |
| Menthol | 0.10 to 0.50 |
| Peppermint oil | 0.10 to 0.50 |
| Sweet almond oil | 0.10 to 0.50 |
| Chamomile extract | 0.10 to 0.50 |
| Cherry bark extract | 0.10 to 0.50 |
| Calendula extract | 0.10 to 0.50 |
| Rosemary extract | 0.10 to 0.50 |
| Citric acid | 0.10 to 0.50 |
| Methylchoroisothiazolinone and methyl-iosothiazolinone[3] | 0.10 to 0.50 |
| Fragrance | 0.10 to 0.50 |

[2]A modified, ethoxylated triglyceride, manufactured by Croda, Inc. of Fullerton, CA
[3]Sold as Kathon ® CG by Rohm and Haas Company, Philadelphia, PA.

Samples of the above formulation were used experimentally on client's hair at a hair dressing salon in the Hollywood area for a some months prior to the submission of this application. Some clients knew that an experimental hair cleansing formulation was being used while others did not. All hair was cleansed as effectively as if a shampoo was used. Clients were uniform in their praise of the effect of this cleanser on their hair. They found that their hair was left shinier, more manageable and with more body that with other shampoo/conditioner combinations they had used. Many wanted to know what the formulation was and when it would be commercially available.

Aloe vera is a humectant. It is included in the formulation for its cleansing and astringent properties. It cools the skin and conditions the hair. Glycerin is another humectant. It has soothing and moisturizing effects. The panthenol is a moisture balancer. The trimethylsilylamodimethacone adds sheen and shine to the hair. The hydrolyzed wheat protein is a conditioning agent. The PEG-60 almond glycerides are an emollient. The menthol has stimulating, cooling and cleansing effects and increases blood circulation. The peppermint oil is cooling and invigorating and causes a soothing effect. It is very effective for greasy hair and skin. The sweet almond oil is an emollient. It is very moisturizing and works effectively on all skin types. The rosemary extract has anti-bacterial properties. It is an astringent and cleans very effectively. The isothiazolinones are biocides which prevent spoilage of the product.

The hair cleanser formulation provided above replaces shampoos and conditioners. The formulation does not contain sodium lauryl sulfate, detergents or other harsh chemicals. When used it does not remove natural oils from the hair and scalp. It does not remove color or dry out the hair.

The hair cleanser has been described with reference to a particular embodiment. Other modifications and enhancements can be made without departing from the spirit and scope of the claims that follow.

What is claimed is:

1. A hair cleanser comprising:
5.00 to 10.00% by weight aloe vera gel;
2.00 to 5.00% by weight glycerin;
1.00 to 3.00% by weight behentrimonium chloride;

1.00 to 3.00% by weight stearamidepropyl dimethyamine;
1.00 to 3.00% by weight cetyl alcohol;
1.00 to 3.00% by weight emulsifying wax;
0.10 to 1.00% by weight panthenol;
0.10 to 1.00% by weight trimethylsilylamodimethicone;
0.10 to 1.00% by weight hydrolyzed whole wheat protein
0.10 to 1.00% by weight PEG-60 almond glycerides;
0.10 to 0.50% by weight menthol;
0.10 to 0.50% by weight peppermint oil;;
0.10 to 0.50% by weight sweet almond oil;
0.10 to 0.50% by weight chamomile extract;
0.10 to 0.50% by weight cherry bark extract;
0.10 to 0.50% by weight calendula extract;
0.10 to 0.50% by weight rosemary extract;
0.10 to 0.50% by weight citric acid;
0.10 to 0.50% by weight methylchoroisothiazolinone and methyliosothiazolinone;
0.10 to 0.50% by weight fragrance; and water.

2. A method of formulating a hair cleanser comprising the steps of:
   a. obtaining:
      aloe vera gel;
      glycerin;
      behentrimonium chloride;
      stearamidepropyl dimethyamine;
      cetyl alcohol;
      emulsifying wax;
      panthenol;
      trimethylsilylamodimethicone;
      hydrolyzed whole wheat protein
      PEG-60 almond glycerides;
      menthol;
      peppermint oil;;
      sweet almond oil;
      chamomile extract;
      cherry bark extract;
      calendula extract;
      rosemary extract ;
      citric acid;
      methylchoroisothiazolinone and methyliosothiazolinone;
      fragrance; and
      water; and
   b. mixing these ingredients in the following proportions
      5.00 to 10.00% by weight aloe vera gel;
      2.00 to 5.00% by weight glycerin;
      1.00 to 3.00% by weight behentrimonium chloride;
      1.00 to 3.00% by weight stearamidepropyl dimethyamine;
      1.00 to 3.00% by weight cetyl alcohol;
      1.00 to 3.00% by weight emulsifying wax;
      0.10 to 1.00% by weight panthenol;
      0.10 to 1.00% by weight trimethylsilylamodimethicone;
      0.10 to 1.00% by weight hydrolyzed whole wheat protein
      0.10 to 1.00% by weight PEG-60 almond glycerides;
      0.10 to 0.50% by weight menthol;
      0.10 to 0.50% by weight peppermint oil; ;
      0.10 to 0.50% by weight sweet almond oil;
      0.10 to 0.50% by weight chamomile extract;
      0.10 to 0.50% by weight cherry bark extract;
      0.10 to 0.50% by weight calendula extract;
      0.10 to 0.50% by weight rosemary extract;
      0.10 to 0.50% by weight citric acid;
      0.10 to 0.50% by weight methylchoroisothiazolinone and methyliosothiazolinone;
      0.10 to 0.50% by weight fragrance; and remainder water.

* * * * *